United States Patent
Brossard et al.

(12) 
(10) Patent No.: US 6,308,749 B1
(45) Date of Patent: Oct. 30, 2001

(54) PROCESS AND DEVICE FOR TRANSFER OF STERILE PRODUCTS BETWEEN A CONTAINER AND AN ISOLATOR

(75) Inventors: Jean-Pierre Brossard, Chatou; Philippe Fontcuberta, Vendone; Jean-Michel Riviere, Villeromain, all of (FR)

(73) Assignee: La Calhene, Velizy Villacoublay (FR)

( * ) Notice: Subject to any disclaimer, the term of this patent is extended or adjusted under 35 U.S.C. 154(b) by 0 days.

(21) Appl. No.: 09/459,512

(22) Filed: Dec. 13, 1999

(30) Foreign Application Priority Data

Jan. 4, 1999 (FR) .................................................... 99 00014

(51) Int. Cl.⁷ ...................................................... B65B 1/04
(52) U.S. Cl. .............................. 141/91; 141/98; 141/383; 422/294
(58) Field of Search ................................. 141/91, 98, 346, 141/348, 383–386; 206/328, 334, 454; 422/292, 294, 302; 53/425, 426

(56) References Cited

U.S. PATENT DOCUMENTS

| | | | |
|---|---|---|---|
| 5,425,400 | * | 6/1995 | Szatmary .................................. 141/98 |
| 5,447,699 | * | 9/1995 | Papciak et al. ......................... 422/294 |
| 5,490,546 | | 2/1996 | Lhoest . |
| 6,030,578 | | 2/2000 | McDonald . |

FOREIGN PATENT DOCUMENTS

| 2 658 489 | 8/1991 | (FR) . |
|---|---|---|
| WO 96/21615 | 7/1996 | (WO) . |

* cited by examiner

Primary Examiner—Steven O. Douglas
(74) Attorney, Agent, or Firm—Pearne & Gordon LLP

(57) ABSTRACT

Sterile products contained in a container (10) are transferred into a sterile isolator (12) by connecting the container onto a lock (28) fitted on the outside of the isolator (12) and equipped with a pulsed light sterilization device (28). The connection between the lock (28) and the isolator (12) is made by a sealed double door transfer device. The throwaway container is equipped with a plug type closer (16), cutout from the inside of the isolator (12) after sterilizing the volume (40) inside the lock (28) and opening the double door (24, 38).

16 Claims, 2 Drawing Sheets

PROCESS AND DEVICE FOR TRANSFER OF STERILE PRODUCTS BETWEEN A CONTAINER AND AN ISOLATOR

DESCRIPTION

1. Technical Domain

The invention relates to a process and a device for transferring previously sterilized products contained in a transport container, into a sterile isolator.

The invention may be used in all industrial fields involving handling of sterile products, and particularly in the pharmaceutical, medical, chemical, food processing industries, etc.

Throughout the rest of this text, the term "products" should be understood in its broadest sense, in other words in particular it covers powders, pellets, components of various shapes and natures, liquids, etc.

2. State of Prior Art

One known manner of transporting previously sterilized products (for example sterilized by gamma irradiation) to an isolator in which any other operations (for example packaging) are to be carried out is to place these products in containers in the form of flexible bags.

One frequently used manner of connecting a container to the isolator and for transferring products inside this isolator is to use connection means with a double door to obtain a sealed transfer. This type of known device comprises a flange normally closed by a door on the container and a flange normally closed by a door on the isolator. When the container is docked onto the isolator, the two flanges are fixed to each other in a sealed manner and the two doors are fixed to each other in a sealed manner. After opening the double door thus formed from the inside of the isolator, the products may be transferred without the need to carry out any prior sterilization operation.

This known technique is safe and is generally satisfactory. However, it has the disadvantage that it is expensive when the transfer frequency is high. Furthermore, the containers have to be either thrown away or recycled after each transfer.

Considering the price of the flange/door assembly fitted on each container, scrapping these containers after use introduces an operating cost that increases as the number of containers used increases.

Furthermore, container recycling operations are also expensive and penalizing when the number of containers used increases. They make it necessary to package flange/door assemblies after use, and then to unpackage them, to make a visual inspection and to clean them before reassembly and to make a new inspection and repackaging.

Another known technique, described particularly in document WO 96 21615, consists of equipping each container with a flange closed by a plug. This can significantly reduce the price of a container so that it can be thrown away after each use. The operating cost of the system thus remains reasonable when the number of transfers increases.

However since it does not use the double door transfer device, this technique has the disadvantage that a non-sterile volume is created after the container is connected onto the isolator, between the plug closing the container and the door closing the isolator.

Document WO 96 21615 proposes to overcome this disadvantage by fitting sterilization means consisting of ultraviolet lamps on the outside of the isolator door. More precisely, the isolator door comes into contact with the inside of the isolator flange in a sealed manner, and after docking the container plug is positioned practically in the same plane as the inside of the isolator flange. The small enclosed volume thus formed between the plug and the door is then sterilized. The isolator door is then opened and the plug is cut out so that products can be transferred.

However, this slystem has some disadvantages.

Thus, since sterilization means are placed in the isolator door, maintenance work (replacing a lamp, electrical repairs, etc.) can only be done after the isolator door is opened and from the inside of the isolator. This creates a major break in the seal and therefore the sterility of the isolator, and the only way to avoid this break is if the work is done in the presence of a container or a special plug designed for this purpose. Moreover, the need to work from inside the isolator is inconvenient.

Furthermore, the sterilization technique using ultraviolet lamps is not very efficient, so that use of the system is limited to relatively small transfer openings.

DESCRIPTION OF THE INVENTION

More precisely, the purpose of the invention is a process for the transfer of sterile products between a container and an isolator in order to overcome the disadvantages of existing processes, by enabling the use of inexpensive throwaway containers while enabling easy maintenance of sterilization means.

The invention achieves this result by means of a process for transferring sterile products between a transport container and a sterile isolator, in which:

the container is docked onto the isolator;
an enclosed volume between the container closer and the isolator closer is sterilized; and
the said closers are opened before starting to transfer the products;

characterized in that the container is docked onto a lock connected on the outside to the isolator and normally separated from it by its closer, the said lock including means of sterilization and delimiting the enclosed volume.

This layout makes it possible to use an inexpensive throwaway container equipped with a simple closer. Furthermore, it enables fast and easy maintenance work on the sterilization means.

In one preferred embodiment of the invention, the lock is fitted to the isolator by means of a sealed double door transfer device, in which the double door forms the isolator closer, before the container is docked onto the lock. This layout means that all sterilization means can be replaced very quickly.

In order to achieve fast and efficient sterilization without limiting the dimensions of the transfer opening, the enclosed volume is preferably sterilized using pulsed light sterilization means placed around a transparent tube delimiting the enclosed volume.

Advantageously, products are transferred after folding a protective sleeve internal to the container over inside the lock.

Preferably, the container closer is opened by cutting out from inside the isolator after opening the isolator closer.

In order to further improve the sterilization efficiency, a container may be used equipped with a closer on which the outside face (which can be turned towards the enclosed volume) is reflecting.

Depending on the case, the container may be connected to the lock either by using a flexible container and docking the container onto the lock using an elastic sleeve, or by using a container with a semirigid flange onto which the container closer is fitted and docking this closer on the lock by fitting the flange into a complementary flange on the lock.

Another purpose of the invention is a device for transferring sterile products between a transport container and a sterile isolator, comprising:

a container closer;

an isolator closer;

means of docking the container onto an isolator, in order to delimit an enclosed volume between the container closer and the isolator closer when docking is complete;

means of sterilizing the said enclosed volume;

the device being characterized in that it also includes a lock connected on the outside to the isolator and normally separated from the isolator by the isolator closer, the said lock including sterilization means and delimiting the enclosed volume.

BRIEF DESCRIPTION OF THE DRAWINGS

We will now describe a preferred embodiment of the invention as a non-restrictive example, with reference to the attached drawings in which.

DETAILED DESCRIPTION OF A PREFERRED EMBODIMENT

Figure 1:
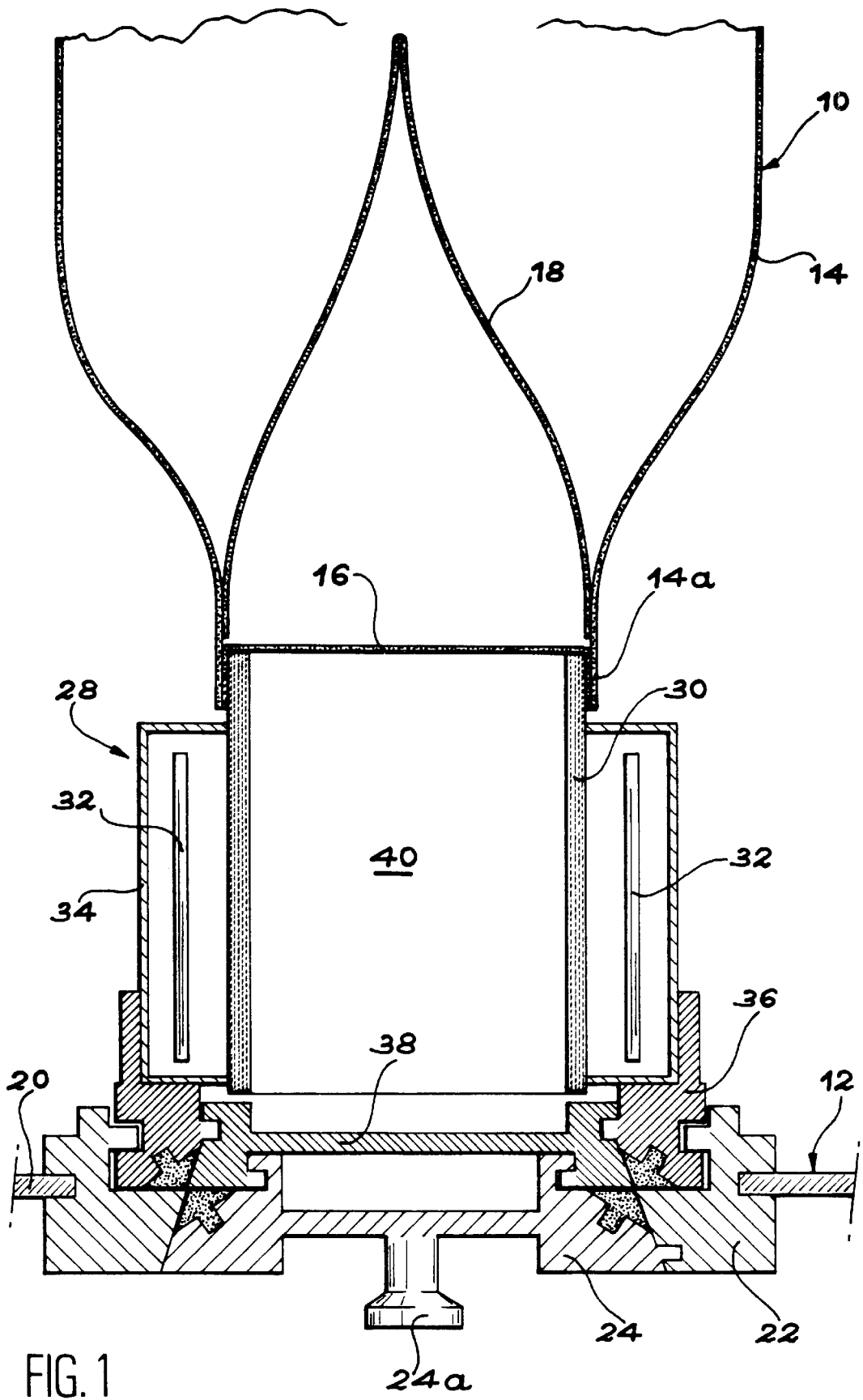
FIG. 1 is a front view diagrammatically showing a sectional view of a transfer device according to one preferred embodiment of the invention.

In FIG. 1, reference 10 denotes a transport container designed to contain sterile products and reference 12 denotes a sterile isolator into which these products are to be transferred (only the part of this isolator to be used for connection of a container is illustrated).

The transport container 10 has a flexible wall 14 in which an opening is formed and which is normally closed by a closer 16. Preferably, the closer 16 is in the form of a plug that can be cut out in order to open the container. For a reason that will be described later, the face of the closer 16 that faces the outside of the container is preferably made to be reflecting, for example by means of metallization.

In the embodiment shown in FIG. 1, the closer 16 is a flexible plug, the peripheral part of which is welded onto an elastic tubular part 14a of the wall 14 delimiting the opening in the container 10.

Furthermore, a protective sleeve 18, also welded onto part 14a of the container wall 14, is normally placed inside this container. This protective sleeve, also made of a flexible material similar to the material of which the wall 14 is made, may be open or closed depending on the case.

Furthermore, the isolator 12 has a wall 20 in which an opening is delimited by a flange 22. This opening is normally closed by a closer 24, which consists of a door which fits into flange 22 in a sealed manner. A handle 24a is used to open the door 24 towards the inside of the isolator 12 when the locking means, for example with bayonet fitting (not shown) are released.

The transport container 10 according to the invention does not dock directly onto the sterile isolator 12, but rather onto a lock 28 connected on the outside to isolator 12.

More precisely, the lock 28 comprises a transparent tube 30, for example made of quartz, and pulsed light sterilization means materialized by lamps 32 distributed uniformly around the tube 30, inside a protective casing 34.

One end of the tube 30 is equipped with a flange 36 delimiting an opening on the inside, normally closed in a sealed manner by a door 38. The door 38 works in cooperation with flange 36 by locking means, for example with bayonet fitting.

The flange 36 is designed to be connected onto flange 22 in a sealed manner, and the door 38 is designed to be connected in a sealed manner onto door 24 when the lock 28 is coupled to the isolator 12 as shown in FIG. 1. Connection means, for example with bayonet fitting, are provided for this purpose between flanges 22 and 36 and between doors 24 and 38. Under these conditions, the assembly formed by flanges 22 and 36 and by doors 24 and 38 forms a sealed double door transfer device in which a sealed transfer can be carried out between the volume 40 delimited inside the tube 30 and inside the isolator 12, when the double door formed by doors 24 and 38 connected to each other is opened.

When lock 28 is coupled to isolator 12, and when container 10 is docked onto lock 28, the enclosed volume 40 delimited between the double door 24, 38 and the closer 16 inside tube 30, may be sterilized by the use of sterilization means 32.

In the embodiment shown in FIG. 1, the end of the transparent tube 30 opposite the flange 36 extends beyond the casing 34 so that the tubular part of the wall 14 of container 10 can be fitted like an elastic sleeve. When this sleeve fitting has been made, the reflecting outside surface of the closer 16 is facing enclosed volume 40 delimited inside the lock 28.

When the device is used in the normal manner, the lock 28 remains connected normally to isolator 12 by means of the double door transfer device composed of flanges 22 and 36 and by doors 24 and 38. When sterile products have to be transferred, a container 10 containing the products to be transferred is docked onto the end of the transparent tube 30 in the manner described above.

When the sealed connection of the container has been made, pulsed light sterilization means 32 are used in order to sterilize the enclosed volume 40 and the surfaces of the plug 16, the door 38 and the tube 30 that delimit this volume. Note that the efficiency of this sterilization is improved by the reflecting nature of the plug 16 facing volume 40. Efficient sterilization can thus be achieved in less than 5 minutes.

When the sterilization is finished, the double door formed by doors 24 and 38 is opened from inside the isolator 12. The operator then cuts out the closer 16 from the inside of the isolator and turns back the protective sleeve 18 inside the lock 28 so as to guide the products to be transferred into the isolator 12, while preventing any direct contact between the products and the internal surfaces of the lock and the sealed double door transfer device. Depending on the case, products may be transferred immediately if the sleeve 18 is opened, or otherwise after cutting out the end of this sleeve.

When the transfer is finished, the double door formed by doors 24 and 38 is closed again and the container 10 is disconnected from lock 28 and then thrown away.

Due to the layout according to the invention, which makes it possible to place sterilization means 32 outside the isolator 12, any work on these sterilization means can be done easily from outside the isolator, for example to replace one of the lamps or to repair an electrical connection.

Furthermore, in the case of a more serious problem, the presence of the double door transfer device between the lock 28 and the isolator 12 makes it easy to replace the lock assembly by a lock equipped with sterilization means in working condition in a particularly short time and therefore in an acceptable manner when a high product transfer rate is required.

Furthermore, the use of pulsed light sterilization means provides particularly fast and efficient sterilization of the volume 40. In particular, this means that products can be transferred through an opening with a large cross-section if necessary. This can also accelerate the throughput through ultraviolet type sterilization means.

Figure 2:
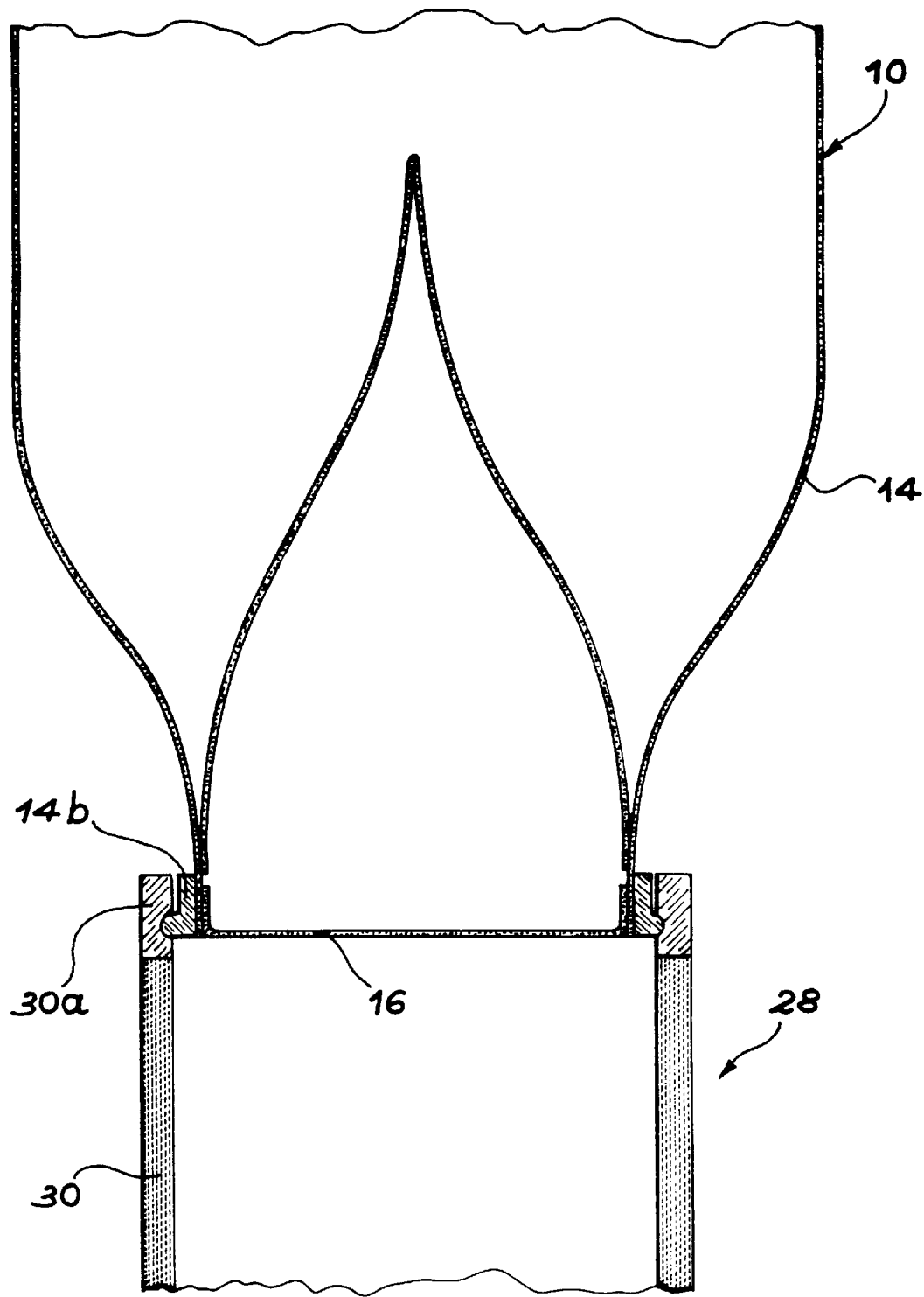
FIG. 2 is a sectional view comparable to FIG. 1 illustrating a variant of the container connection onto the lock.

FIG. 2 diagrammatically illustrates a variant embodiment of the invention. This variant differs from the embodiment in FIG. 1 essentially by the means of docking container 10 onto lock 28.

Thus in this case, the tubular elastic part 14a of the wall 14 of container 10 is replaced by a semi-rigid flange 14b. This flange 14b supports closer 16. Its outside surface includes a projecting part that can be force fitted into a recessed part formed inside a flange 30a fitted onto the corresponding end of the transparent tube 30 of lock 28.

All other characteristics of the device and the process for using it are identical to the characteristics described above with reference to FIG. 1.

Obviously, the invention covers all variants and is not restricted to the embodiments described above as examples.

What is claimed is:

1. A process for transferring sterile products between a transport container and a sterile isolator, comprising the steps of:
   docking the container onto the isolator;
   sterilizing an enclosed volume formed between closers provided on the container and the isolator; and
   opening said closers before starting to transfer the products;
   wherein the container is docked onto a lock connected on an outside of the isolator and normally separated from the isolator by said isolator's closer, said lock including sterilization means and delimiting the enclosed volume.

2. Process according to claim 1, in which before the container (10) is docked onto the lock (28), the lock is connected onto the isolator (12) by means of a sealed double door transfer device, in which the double door (24, 38) forms the closer of the isolator (12).

3. Process according to either of claims 1 and 2, in which the enclosed volume (40) is sterilized using pulsed light sterilization means (32) placed around a transparent tube (30) delimiting the said enclosed volume.

4. Process according to claim 1, in which the products are transferred after turning a protective sleeve (18) internal to the container (10), over inside the lock (28).

5. Process according to claim 1, in which the closer (16) of the container (10) is opened by cutting out from the inside the isolator (12), after opening the isolator closer (24, 38).

6. Process according to claim 1 in which the closer on the container has an outside face that can face the enclosed volume (40) and is reflecting.

7. Process according to claim 1 in which the container is flexible and the container is docked onto the lock (28) by an elastic sleeve fitting.

8. Process according to claim 1 in which the container (10) has a semi-rigid flange (14b) supporting the closer (16) of the container (10), and the container is docked onto the lock (28) by fitting the flange (14b) into a complementary flange (38) on the lock.

9. A device for transferring sterile products between a transport container and a sterile isolator, said device comprising:
   a container closer;
   an isolator closer;
   means of docking the container onto the isolator, in order to delimit an enclosed volume between the container closer and the isolator closer when docking is complete;
   sterilization means for sterilizing said enclosed volume; the device further including a lock connected on an outside to the isolator and normally separated from the isolator by the isolator closer, said lock including the sterilization means and delimiting the enclosed volume.

10. Device according to claim 9, in which the isolator closer comprises a double door (24, 38) of a sealed double door transfer device inserted between the lock (28) and the isolator (12).

11. Device according to any one of claims 9 and 10, in which the lock (28) comprises a transparent tube (30) delimiting the enclosed volume (40) between the container and isolator closers (16; 24, 38), the sterilization means (32) being used consisting of pulsed light sterilization means surrounding the transparent tube (30).

12. Device according to claim 9, further comprising a protective sleeve (18) internal to the container (10) that can be turned over inside the lock (28) when docking is complete, and the container and isolator closers (16; 24, 38) are open.

13. Device according to claim 9, in which the container closer (16) can be cut out from inside the isolator (12).

14. Device according to claim 9, in which the container closer (16) has a reflecting outside surface designed to face the enclosed volume.

15. Device according to claim 9, in which the container (10) has a flexible wall (14), the docking means including an elastic part (14a) of the wall, surrounding the container closer (16) and that can be fitted like a sleeve onto the lock (28).

16. Device according to claim 9, in which the container (10) has a semi-rigid flange (14b) on which the container closer (16) is fitted, and the lock (28) has a flange (30a) complementary to the container flange, and in which the container flange may be inserted to form docking means.

* * * * *